(12) United States Patent
Prescott

(10) Patent No.: US 7,371,399 B2
(45) Date of Patent: May 13, 2008

(54) POLYMER GEL CONTAINING HYALURONIC ACID AND COLLAGEN, AND ITS USE IN JOINTS

(76) Inventor: Albert G. Prescott, 16 Lake Shore Dr. North, Westford, MA (US) 01886

( * ) Notice: Subject to any disclaimer, the term of this patent is extended or adjusted under 35 U.S.C. 154(b) by 244 days.

(21) Appl. No.: 11/181,107

(22) Filed: Jul. 14, 2005

(65) Prior Publication Data

US 2006/0018946 A1    Jan. 26, 2006

Related U.S. Application Data

(60) Provisional application No. 60/590,517, filed on Jul. 23, 2004.

(51) Int. Cl.
*A61F 2/30* (2006.01)
(52) U.S. Cl. .................................... 424/422
(58) Field of Classification Search ............... 530/356
See application file for complete search history.

(56) References Cited

U.S. PATENT DOCUMENTS

| 4,472,376 A | * | 9/1984 | Kamishita ................... 514/3 |
| 4,592,864 A | * | 6/1986 | Miyata et al. ............... 530/356 |
| 4,636,524 A | * | 1/1987 | Balazs et al. ................ 514/781 |
| 5,137,875 A | * | 8/1992 | Tsunenaga et al. ........... 514/21 |

OTHER PUBLICATIONS

Kawasaki et al. Hyaluronic Acid Enhances Proliferation and Chondroitin Sulfate Synthesis in Cultured Chondrocytes Embedded in Collagen Gels. Journal of Cellular Physiology. 1999. vol. 179, pp. 142-148.*
Speranza et al. Influenced of Fibronectin on the Fibrillogenesis of Type I and Type III Collagen. Collagen Related Research. 1987. vol. 7, No. 2, pp. 115-123.*
Nagoski et al. A Study of Collagen-Hyaluronan Interaction Through Swelling in Polyacrylamide Gels. Research in Communications in Molecular Pathology and Pharmacology. 1995. vol. 89, No. 2, pp. 179-188.*
V&P Scientific, Lt. Table of Viscosity Measurements. No date.*
Cells Tissues Organs 2001; 169:248-256.
Cells Tissues Organs 2001; 169-257-264.

* cited by examiner

*Primary Examiner*—Nashaat T. Nashed
*Assistant Examiner*—William W. Moore
(74) *Attorney, Agent, or Firm*—Kerri P. Schray; Brian M. Dingman; Mirick, O'Connell, DeMallie & Lougee, LLP

(57) ABSTRACT

Formulations and methods for treating joints, such as temporomandibular joint disorders, osteoarthritis of the knee, hip and other types of inflammatory joint diseases. The method involves identifying specific matrix metalloproteinases (MMPs) that may be responsible for degrading the soft tissues of the joint in question, identifying the specific component of the joint the MMP(s) are targeting, and injecting a polymer gel with the component the MMP(s) seek to destroy, thus preserving the joint and allowing time to heal. These formulations typically require a mixture of glycosoaminoglycans and collagen proteins. One formulation in particular includes both hyaluronic acid and at least type I collagen.

5 Claims, 1 Drawing Sheet

POLYMER GEL CONTAINING HYALURONIC ACID AND COLLAGEN, AND ITS USE IN JOINTS

CROSS REFERENCE TO RELATED APPLICATION

This application claims priority of Provisional application Ser. No. 60/590,517, filed on Jul. 23, 2004.

STATEMENT OF GOVERNMENT SUPPORT

This invention was made with the support of the United States government under grant number R43DE14504-01A2, awarded by the National Institutes of Health. The government has certain rights in the invention.

FIELD OF THE INVENTION

This invention relates to formulations and methods for treating joint pain associated with inflammatory, degenerative and other joint diseases.

BACKGROUND OF THE INVENTION

The National Institutes of Health estimates that over 7 million people suffer from chronic pain specifically related to the temporomandibular (TM) joint. Despite this, there are very few proven effective therapies, especially for patients who do not respond to over the counter anti-inflammatory drugs. Based on the published literature, it is believed that the disease cycle involves injury, followed by the production of inflammatory cytokines, followed by the over expression of matrix metalloproteinases, and resulting in degradation of tissues. This degradation in turn produces inflammation, which leads to the expression of more cytokines; the cycle becomes more and more destructive.

It is estimated that over $1 billion is spent by Americans to deal with TMD pain. Of the 7 million people suffering TMD, 2 million will seek medical help. 100,000 people will undergo some sort of surgical procedure. The average age of symptom onset is 18-26 years old. Women are more likely to suffer chronic facial pain and TMD than men by 2:1. Women are 10 times more likely than men to pursue medical help, including surgery.

Current treatment phases include:

Phase 1: Educating the patient about muscle fatigue. Improvement of oral hygiene is stressed. This includes no gum chewing, candy chewing, jaw clenching etc. Soft diets are recommended and non-steroidal anti-inflammatories (NSAIDs) such as ibuprofen and muscle relaxants of the benzodiazepine class are prescribed. Typically only 50% of patient will improve at this stage. The rest progress to Phase 2.

Phase 2: Continuation of NSAIDs and benzodiazepine. A bite splint is usually prescribed to improve the joint occlusion. Typically, of the 50% from phase 1 that did not improve, only 25% of patients will improve during this phase. The rest progress to Phase 3.

Phase 3: Continuation of NSAIDs and a splint. Ultrasonic therapy, electrogalvanic stimulation or biofeedback is added to the treatment regiment. No one of the mentioned treatments has been shown to be better than the other. Of the patients who progress to this phase, less than 15% improve. The rest progress to Phase 4.

Phase 4: A series of approaches such as steroid injections, physical therapy, psychological counseling, and eventually, surgery. Less than 50% of these patients improve.

The treatment regiment is essentially, NSAIDs, progression into cortisone injections, followed by surgery. The shortcomings of these methods are as follows:

NSAIDs only help about 50% of the patient who use them.

Cortisone and other steroids injected into the soft tissues of the TM joint have been shown to have a deleterious effect on the soft tissues. Though pain subsides after a steroid injection, the steroid causes degradation and eventually failure of the TM joint.

Surgery is expensive, invasive, and does not guarantee success in treating pain.

Polymer gels are currently used to treat pain in various cases of osteoarthritis (OA) of the knee. Three products, SYNVISC® Hylan GF-20 (Genzyme Corporation. Cambridge, Mass.), HYALGAN® Sodium Hyaluronate (Sanofi-Aventis U.S. LLC. New York. N.Y.), and SUPARTZ® Joint Fluid Therapy (Smith & Nephew plc, London, England) have all received FDA approval for treatment of OA in patients who do not respond to NSAIDs. Of these three, SYNVISC® Hylan GF-20 is the most widely used, with sales that currently exceed $127 million annually. Current gels used to treat pain associated with OA of the knee use almost pure solutions of hyaluronic acid (HA), a biological polymer that is native to all mammalian connective tissue. For example, SYNVISC® Hylan GF-20 includes 0.8% HA. Despite their success for treatment of OA of the knee, these products have not been used successfully to treat temporomandibular joint disorders (a.k.a. TMJ or TMD).

The TM joint differs from the knee in several respects. First, from a mechanical perspective, the knee is essentially a "hinge" joint with only two modes of motion: extension and flexion. The TM joint has three modes of motion including elevation/depression, protrusion/retraction, and lateral deviation. In this respect, the TM joint is far more complex than the knee.

The TM joint also appears to handle forces far in excess of the knee joint. Researchers designing knee replacement devices (ACLs, fixation devices, etc.) typically find that in vitro testing of these devices yields force values of 200 to 400 Newtons. In vivo testing yielded 300 Newtons. Bite forces in men and women have been reported at 847 and 597 Newtons respectively.

The TM joint also varies from the knee physiologically. Though both joints are comprised of water, chondrocytes, collagen protein, and glycosoaminoglycans (GAGs), the relative ratios of these materials are very different. Whereas the knee is comprised of Type II collagen (>95% of the total collagen in the knee), the TM joint is mostly Type I collagen, with some Type III collagen. Both the knee and TM joint have GAGs present, the most abundant being chondoitin sulfate, which accounts for about 80% of the GAGs of these joints, but the TM joint's hyaluronic acid concentration tends to be only 5% of GAGs, while the hyaluronic acid concentration in the knee ranges from 10-15% of the GAGs.

In the knee, where the hyaluronic acid concentration relative to the water content is about 1%-1.5%, it is easy to understand why the commercial products that are used to treat OA of the knee tend to be in the 10-15 mg/ml range (1%=10 mg/ml). For example, HYALGAN® Sodium Hyaluronate is 10 mg/ml hyaluronic acid, and SYNVISC® Hylan GF-20 is 8 mg/ml. It is also easy to understand why simply using these products in the treatment of ID/OA TMD may not be successful since they do not take into account the unique characteristics of the TM joint.

In the knee, products comprised of hyaluronic acid appear to slow the progression of early stage OA. It is believed this is due to two possible factors. First, it is widely held that hyaluronic acid's role is mostly mechanical, hence its classification as a medical device. Repeated injection into the knee delivers moisture which is typically lacking in OA tissues, and acts as a physical barrier to the inflammatory chemicals that OA tissues tend to release. Also, since low molecular weight oligosaccharides tend to be markers of OA, it is thought that high molecular weight HA can be re-incorporated into the extracellular matrix of cartilage tissue.

A less popular theory is that the inflammatory chemicals released by OA tissues have significant hyaluronidase activity, and are part of a cycle of destruction in OA tissues resulting in low molecular weight oligosaccharides. If this is the case, hyaluronic acid injections not only provide a physical barrier to inflammatory agents, but may also serve to redirect the activity of these agents by providing excess (sacrificial) substrate for them to consume. As inflammation reduces, less of these chemicals are produced by the OA tissues, and the destructive cycle is broken, or at least slowed to a manageable rate.

Since the HA concentration in the TM joint is about half what it is in the knee, it should come as no surprise that Bertolami et al. observed that injections of HA in OA TM joints had little or no beneficial effect, while injections in patients with reducing displaced disk (DDR) noted a reduction in pain. Clearly these HA injections were providing a physical benefit such as delivery of moisture and possibly a physical barrier in the DDR patients. Straight HA did not provide the full benefit noted by patients with OA of the knee.

This difference between the efficacy of the HA in the knee and TM joint can potentially be explained by examining the latest biochemical research on the TM joint published in *Cells Tissues Organs,* Volume 169, No. 3, pp. 248-264. Two articles have for the first time described the inflammatory agents and degenerative pathways of these agents. In particular, Puzas et al., and Kacena et al., detail the role of inflammatory cytokines such as IL-1β, TNF-α and their expression of matrix metalloproteinases (MMPs). Kacena clearly showed that human patients who suffered TMJ disorders had significantly elevated level of both IL-1β and TNF-α in their TM joint synovial fluid.

IL-1β and TNF-α bind to the AP-1 binding sites. These sites regulate the production of MMPs 1, 3, 9, and 10. Puzas et al. showed in their study of a mouse model with OA of the TM joint, that not only were the cytokines present, but many of the MMPs were present also. In particular, a Zymographic analysis of the MMP activity in the TMJ disc cells of the mouse showed that MMPs in the molecular weight range close to 58 kD were present. This was a very intense band that appeared to vary between the molecular weights of 50 to 60 kD. This band corresponds to MMP1 (MW=57-52 kD), MMP3 (MW=55-60 kD) and MMP10 (MW=55-60 kD). All of these MMPs have hyaluronidase activity. MMP1 has a very specific type I collagenase activity.

Given the state of the art, there is a definite need for a novel composition to treat joint pain such as TMJ and other inflammatory and degenerative joint diseases.

SUMMARY OF THE INVENTION

It is theorized that the presence of over regulated MMPs, particularly MMP1, in inflamed TM joint tissues causes the breakdown of at least both the type I collagen and hyaluronic acid. For this reason, injections that are pure hyaluronic acid have little effect on degenerated TM joint tissues.

This invention includes methods for treating TMD using a formulation designed specifically for the TM joint. The formulation comprises a minimally invasive polymer gel that provides mechanical lubrication, a physical barrier to cytokines, and a sacrificial substrate for matrix metalloproteinases, to break the cycle of destruction and aid in the healing process.

There are very few minimally invasive methods for treating TM disease (TMD). The invention provides for a polymer gel that will treat internal derangement/osteoarthritis (ID/OA) TMD pain. This will provide an additional option for patients and doctors when deciding on a course of treatment.

The preferred embodiment of the inventive polymer gel comprises at least high molecular weight (preferably greater than 1 million daltons) hyaluronic acid, and soluble type I collagen. The gel is designed to remain in the TM joint longer than pure HA products. As opposed to most medical grade collagens, which are Type II, the inventive gel can comprise soluble Type I and Type III collagens, which are major components of the TM joint.

It is likely that several issues will be addressed by this invention. First, the residence time in the TM joint will be higher, both due to the significantly higher viscosity and the longer half-life associated with HA-collagen mixtures versus pure HA. A longer residence time should equate to greater efficacy. Second, biological processes that specifically destroy the type I collagen that make up the articular disk, or meniscus, can be re-directed to the injection. This allows the destructive cycle to be broken and also increases the efficacy of the material.

The invention further includes a method for formulating polymer gel formulations that interrupt the destructive cycle of joint disease by interacting with the MMP(s) responsible for inflammation and pain, and the resulting formulations per se, as well as their use. To design such a polymer formulation, the disease cycle is identified. Inflammatory cytokines are then identified, and the resulting matrix metalloproteinase (MMP) enzymes present in the joint are determined. Once these MMP(s) have been determined, their enzymatic substrates are identified. Once this is accomplished, a polymer gel to treat the disease may be formulated.

A first embodiment of the invention comprises a formulation comprising polymer gel to treat TMJ disorders. The formulation may comprise hyaluronic acid and type I collagen, and may further comprise type III collagen. The formulation preferably comprises approximately 1.5% hyaluronic acid, approximately 1.5% total collagen comprising type I and type III collagens, approximately 96% water and approximately 0.9% NaCl. The hyaluronic acid is preferably of a high molecular weight of more than one million Daltons.

The invention further features a method of treating a joint comprising placing into the joint the above-described formulation. The formulation may be placed into the joint by injection. Also featured is a method for treating joint pain, in which inflammatory cytokines are present in the joint at elevated levels, comprising identifying one or more inflammatory cytokines present in the joint at elevated levels, determining one or more resulting matrix metalloproteinase (MMP) enzymes present in the joint, formulating a polymer gel comprising one or more substrates that said MMP enzymes are active against, and placing the polymer gel into the joint. The polymer gel may comprise hyaluronic acid and at least type I collagen. The polymer gel preferably comprises at least about 1% hyaluronic acid, at least about 1% total collagen comprising type I and type III collagens.

BRIEF DESCRIPTION OF THE DRAWINGS

Other objects, features and advantages will occur to those skilled in the art from the following description of the preferred embodiments, and the accompanying drawings, in which.

DETAILED DESCRIPTION OF THE PREFERRED EMBODIMENTS

The following is a description of the preferred embodiment of the invention. In the following examples, a prototype formulation was developed using the inventive methodology, and then tested on an animal model.

EXAMPLE 1

Polymer Gel to Treat TMJ Disorders

Samples of synovial fluid from TM joints of patients suffering TMJ pain have been analyzed. Kacena et al. clearly showed that human patients who suffered TMJ disorders had significantly elevated level of both IL-1β and TNF-α in their TM joint synovial fluid.

IL-1β and TNF-α bind to the AP-1 binding sites. These sites regulate the production of MMPs 1, 3, 9, and 10. Puzas et al. showed in their study of a mouse model with OA of the TM joint, that not only were the cytokines present, but many of the MMPs were present also. In particular, Puzas et al. presented a Zymographic analysis of the MMP activity in the TMJ disc cells of the mouse, which showed that MMPs in the molecular weight range close to 58 kD were present. This was a very intense band that appeared to vary between the molecular weights of 50 to 60 kD. This band corresponds to MMP1 (MW=57–52 kD) and MMP3 (MW=55–60 kD) and MMP10 (MW=55–60 kD). All of these MMPs have hyaluronidase activity. MMP1 has a very specific type I collagenase activity.

Subsequently, a polymer gel was formulated that comprises high molecular weight (greater than 1 million daltons) hyaluronic acid and at least soluble type I collagen. The formulation was designed to remain in the TM joint longer than pure HA products. As opposed to most medical grade collagens, which are Type II, this formulation included a soluble collagen mixture including Type I and Type III collagens, both of which are important components of the TM joint. The composition of the gel formulation was as follows: approximately 1.5% HA, approximately 1.5% Semed S product from Kensey Nash Corp, Exton, PA (which contains soluble Type I and III collagens), approximately 96.13% water, and approximately 0.87% NaCl. The formulation had a viscosity of 6476 centipoise when measured at 0.5 rpm with a CP-52 spindle on a Brookfield viscometer. In contrast, the HYALGAN® Sodium Hyaluronate product had a viscosity of 500 centipoise when measured under the same conditions. In the figures, this inventive formulation is labeled "NINJA."

Testing of this Formulation

There are two types of data presented, diagnostic and clinical. The diagnostic data (FIG. 1) is comprised of CT scans of miniature pig animal models. All CT scans shown are of the transverse plane viewed in the caudal direction.

Figure 1:
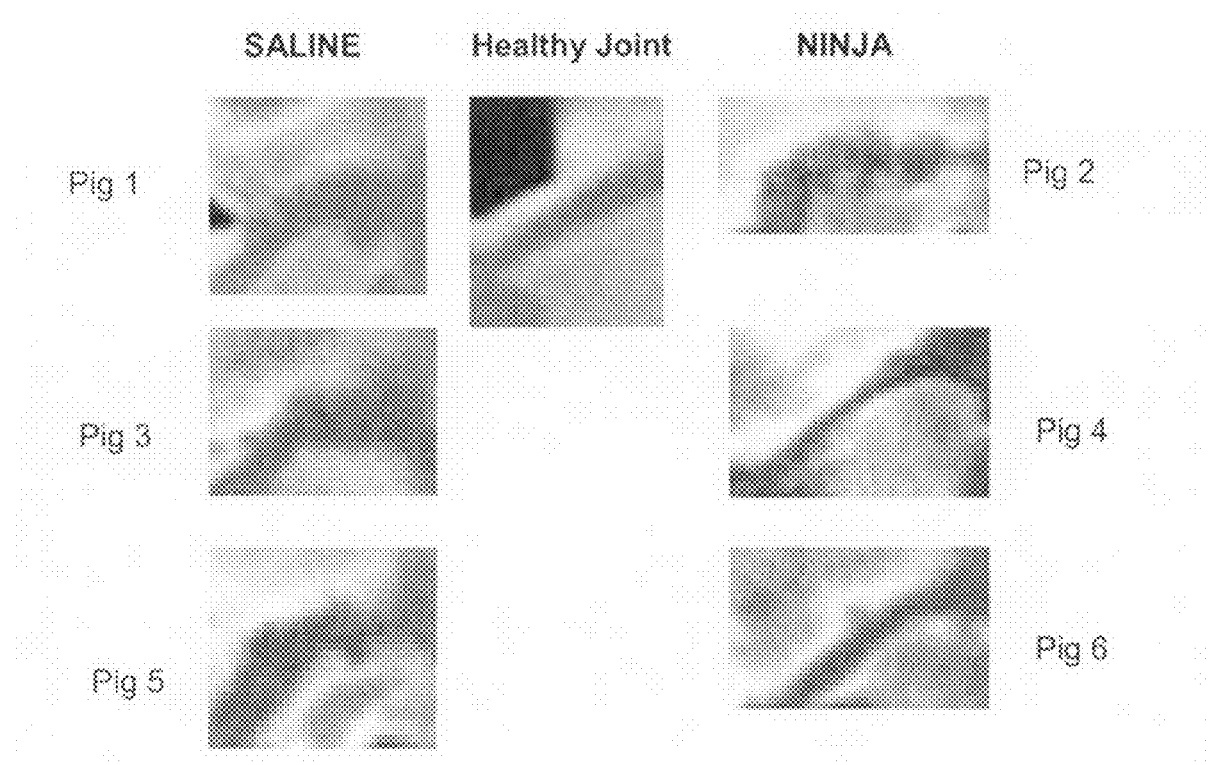
FIG. 1 includes CT scans of the TM joints of animal models, illustrating the efficacy of the inventive formulation in treating the TM joint.

The view in the middle column is of a healthy TM joint. The two main articular surfaces of the temporal bone and the mandibular condyle are visible. The space between is occupied by the meniscal disk, which remains invisible in a CT scan. The surgical model used to test the invention was a surgical defect to the temporal bone. The left column of FIG. 1 shows CT scans of three TM joints with the surgical defect imparted. The articular surface of the temporal bone is noticeably rough compared to the control. In addition, the articular surface of the mandibular condyle is also rough, illustrating a disease progression.

Once this defect was imparted, two groups of animals were treated by injection into the TMJ. The first group (left column) was treated with a saline placebo, while the second group (right column) was treated by injection into the joint of one milliliter of the inventive polymer gel. The placebo results are shown in the figure; pigs 1, 3 and 5. In the figure, the surgical defects are all visible on the temporal bone. In addition, all three TM joints show disease progression to the mandibular condyle.

Conversely, of the three animals treated with the inventive polymer gel (pigs 2, 4 and 6), only one animal (pig 2) shows a disease progression, while the other two show only the surgical defect, a 67% improvement over the placebo group.

Figure 2:
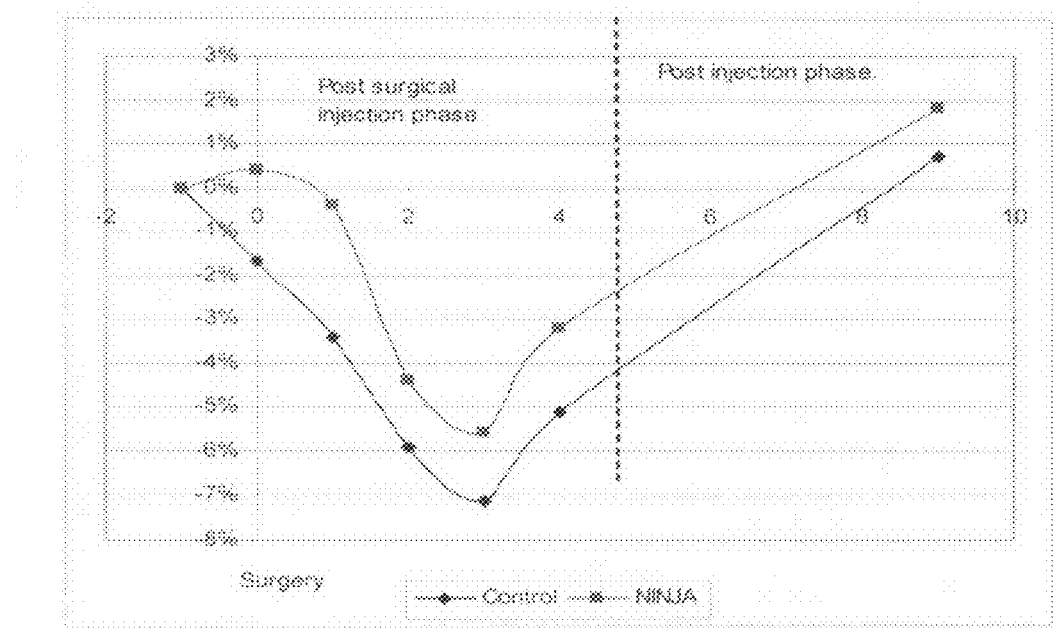
FIG. 2 is a graph of animal weight, which further supports the efficacy.

A graph of relative body weight changes of these pigs over the course of 9 days is shown in FIG. 2. Drops in body weight represent pain. In all cases, the group treated with the inventive polymer gel (termed "NINJA") show less body weight loss than the placebo treated group, which establishes that this treatment measurably reduces pain.

What is claimed is:

1. A gel formulation to treat temporomandibular joint (TMJ) disorders comprising approximately 1.5% hyaluronic acid, and approximately 1.5% total collagen comprising type I and type III collagen, approximately 96% water, and approximately 0.9% NaCl, wherein the formulation has a viscosity of about 6476 centipoise (cP).

2. The formulation of claim 1, wherein the hyaluronic acid is of a high molecular weight of more than one million Daltons.

3. A method of treating a joint comprising placing into the joint the formulation of claim 1.

4. The method of claim 3 wherein the formulation is placed into the joint by injection.

5. A method for treating joint pain, in which inflammatory cytokines are present in the joint at elevated levels, comprising:
  (i) identifying one or more inflammatory cytokines present in the joint at elevated levels;
  (ii) determining one or more resulting matrix metalloproteinase (MMP) enzymes present in the joint;
  (iii) preparing a polymer gel according to the formulation of claim 1, comprising one or more substrates that said MMP enzymes are active against; and
  (iv) placing the polymer gel into the joint.

* * * * *